(12) United States Patent
Hart et al.

(10) Patent No.: US 6,626,861 B1
(45) Date of Patent: *Sep. 30, 2003

(54) BALLOON CATHETER APPARATUS AND METHOD

(75) Inventors: Charles C. Hart, Summerville, NC (US); Eduardo Chi-Sing, Dana Point, CA (US); Frans Vandenbroek, Rancho Santa Margarita, CA (US); Richard L. Myers, Coto de Caza, CA (US)

(73) Assignee: Applied Medical Resources, Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/403,860

(22) PCT Filed: Apr. 22, 1998

(86) PCT No.: PCT/US98/07772

§ 371 (c)(1),
(2), (4) Date: Oct. 4, 2000

(87) PCT Pub. No.: WO98/50101

PCT Pub. Date: Nov. 12, 1998

(51) Int. Cl.$^7$ ................................................ A61M 29/00
(52) U.S. Cl. .................................................... 604/96.01
(58) Field of Search ...................... 606/198; 604/96.01, 604/97.01, 99.01, 101.01, 101.02, 103, 103.01–103.02, 103.05, 103.07–103.08, 103.13, 104

(56) References Cited

U.S. PATENT DOCUMENTS

| | | | | |
|---|---|---|---|---|
| 4,819,751 A | * | 4/1989 | Shimada et al. | 604/104 |
| 5,662,713 A | * | 9/1997 | Andersen et al. | 128/898 |
| 5,868,708 A | * | 2/1999 | Hart et al. | 604/101.05 |
| 5,954,741 A | * | 9/1999 | Fox | 606/198 |

* cited by examiner

Primary Examiner—Brian L. Casler
Assistant Examiner—Mark K Han
(74) Attorney, Agent, or Firm—Richard L. Myers (57) ABSTRACT

A surgical device for cleaning and removing obstructing material from within a vascular conduit or other bodily passageway. The device comprises a balloon catheter having an independently operable outer woven sleeve having a plurality of mesh openings. The woven sleeve surrounds the radially expandable and contractible balloon. In one embodiment, the outer woven sleeve is configured into a predetermined shape through manipulation of the catheter and used to maintain the inflated balloon within that predetermined configuration. In another embodiment, the woven sleeve is radially expanded by the inflated balloon such that the woven mesh is driven into the vascular conduit. The woven sleeve may be used to abrade the surface of the vascular conduit and increase the flow passage or alternatively as traction for various other surgical procedures within the vascular conduit.

39 Claims, 5 Drawing Sheets

BALLOON CATHETER APPARATUS AND METHOD

FIELD OF THE INVENTION

This invention relates generally to surgical devices and more particularly, to an improved balloon catheter apparatus and method for enlarging a flow path within a vascular conduit or other body passageway.

BACKGROUND OF THE INVENTION

Catheters having inflatable balloons affixed to their leading edge are commonly used in a variety of surgical applications. One application for such a "balloon catheter," is for dilating blood vessels which have been partially or entirely blocked by deposits or other obstructions. The balloon catheter is introduced into the affected blood vessel and the deflated balloon is maneuvered into a blocked or otherwise obstructed flow path within the vessel. By inflating the balloon, the deposits or obstructions are compressed against the inner wall of the vessel, thereby enlarging the flow path. Other applications include the removal and/or compression of adherent materials such as atherosclerotic plaque, thrombosis, stenosis, occlusions, clots, stones, and other potentially obstructive material from within vascular conduits and other body passageways.

Prior devices used in such applications include catheters having a catheter shaft and an inflatable balloon located near the leading or distal end of the catheter. The balloon of such a catheter usually consists of an inflatable sleeve or bulb fitted on the outside of the tubular catheter shaft. The balloon is inflated by the infusion of a fluid into the balloon chamber from within the shaft. It is important that the balloon's inflation be controlled, such that it is not overinflated, resulting in an overexpanded balloon which can rupture or otherwise damage the affected vascular conduit or other body conduit.

In an effort to reduce the dangers of over expansion and thus, potential damage to the conduit, modem catheters are commonly configured with reinforced balloons that can only expand to a predetermined maximum diameter, regardless of the interior pressure applied. While effective at limiting the radial expansion of the associated balloon, these catheters are only effective when used within a vascular or other conduit of a specified size. Conduits having different or changing diameters may require the use of a number of such catheters, each having a specified maximum balloon diameter. In addition, many applications could benefit from a balloon having a specific configuration or shape for use within the conduit. These specific shapes or configurations could advantageously be used to compress or remove occluding material, for infusing treatment fluids as well as for therapeutic effects. Thus, there is a need for a balloon catheter which can restrain the maximum radial expansion of the inflated balloon and can also configure the inflated balloon to a specified shape or configuration. There is also a need for such a balloon catheter which has the ability to limit the radial expansion of the inflated balloon to a number of different maximum radial diameters.

When removing occluding material from within a vascular conduit, such as a blood vessel, it is important that the surface of the balloon catheter be relatively smooth in order to prevent damage to the inner lining. Prior art balloon catheters are generally provided with a smooth outer surface for this purpose. However, it is often desirable to have an abrasive outer surface for contacting the inner walls of the vascular conduit. The abrasive outer surface allows for improved removal of the occluding material as well as for traction. In addition, there is also a need for a balloon catheter having a more abrasive outer surface for use in other applications such as the removal of thrombus or other obstructions from within an artificial graft. These applications often require more intense scrubbing. Thus, there is a need for a balloon catheter which has an abrasive outer surface, yet which is not damaging to the inner lining of the vascular conduit or other conduit. There is also a need for such an abrasive outer surface that retains a consistent abrasiveness regardless of the balloon's inflation or expansion. There is also a need for a balloon catheter which includes an abrasive outer surface suitable for removing thrombus or other occluding material from within an artificial graft.

SUMMARY

The present invention overcomes these problems of the past by providing a surgical device having a coaxial overstructure or outer sleeve which is operable independently of an internally disposed balloon or bladder. By using an outer sleeve, which is independent of the generally surrounded balloon, and which is radially expandable and collapsible through actuation of the surgical device, the maximum radial and axial expansion of the inflated balloon can be controlled. In addition, the use of an outer sleeve which is independently expandable into a number of predetermined configurations, allows the balloon to be constrained within a plurality of different sizes and shapes. The surgical device of the present invention is thus, capable of conforming to a plurality of different body conduits and sizes without the need to change to a different size surgical device. The surgical device of the present invention also solves the need for a device which can control the size and shape of an internal balloon or bladder regardless of the application.

The present invention also satisfies the need for a surgical device which provides traction within a vascular conduit or other passageway by providing a balloon catheter having an independent outer sleeve. The outer sleeve is preferably configured with an abrasive or tractive outer surface for contact against the inner walls of the conduit. The outer sleeve is advantageously made from a woven mesh material which can be expanded and collapsed into a number of predetermined shapes and sizes. The balloon may be inflated to conform to the outer sleeve and may be constrained within the predetermined configuration of the mesh sleeve. Fluid pressure may be increased within the balloon to increase traction with the wall of the conduit. In addition, the mesh sleeve may also be utilized to limit the overall length of the inflated balloon.

The present invention also satisfies the need for a surgical device which may be used for cleaning and removing obstructions and clots from within an artificial graft by providing a balloon catheter having an independent mesh sleeve with an abrasive outer surface. For purposes of this disclosure, an artificial graft or shunt is considered a vascular conduit and all discussions relating to vascular or other body conduits shall include artificial grafts, shunts and similar passageways.

By providing a balloon catheter which utilizes procedures similar to those of the prior art balloon embolectomy catheters, a surgeon can effectively use the balloon catheter of the present invention without the need to learn new or additional procedures. The balloon catheter of the present invention includes an outer mesh sleeve made from a woven filament which is connected to the catheter at one end, either proximally or distally of the balloon, and which has an irregular outer surface. Inflation of the balloon expands the outer mesh sleeve and compresses the filament mesh into the obstructing material.

The present invention is generally directed to an improved balloon catheter for enlarging a flow passage within a vascular conduit or other body passageway. The improved balloon catheter includes a catheter tube which has a longitudinal axis which extends between a proximal end and a distal end. An elongate inner member may be disposed coaxially within the catheter tube. Preferably, this inner member is longitudinally slidable within the catheter tube and configured such that a longitudinal passageway is created between the inner member and the catheter tube for passage of a fluid.

An inflatable and deflatable balloon is disposed coaxially about a distal end of the inner member. The balloon includes a proximal balloon end which is connected to the distal end of the catheter tube and a distal balloon end which is connected to the distal end of the inner member to define an annular balloon chamber or cavity. The annular balloon chamber is fluidly connected with the longitudinal passageway. The balloon is preferably a conventional catheter balloon which is distensible and includes properties for inflating and deflating in response to a fluid passed through the longitudinal passageway.

Alternatively, the balloon ends may only be connected to the inner member. In this configuration, the proximal balloon end is connected to the inner member and the distal balloon end is connected to the distal end of the inner member, distally from the proximal balloon end, to define the annular balloon chamber. A longitudinal passageway extends axially through the inner member and is fluidly connected through an opening within the annular balloon chamber. As previously discussed, the balloon is preferably a conventional catheter balloon and includes properties for inflating and deflating in response to a fluid passed through the longitudinal passageway in the inner member.

An independent outer sleeve is coupled to the catheter and generally surrounds the balloon. The outer sleeve includes a proximal sleeve end which is connected to the distal end of the catheter tube and a distal sleeve end which is connected adjacent the distal end of the inner member distally from the distal balloon end. The outer sleeve is radially expandable into at least one predetermined configuration and size and also collapsible to a minimum radial diameter through longitudinal movement of the inner member relative to the catheter tube. Preferably, the outer sleeve comprises a tubular mesh of a woven or braided filament. The mesh sleeve is configured with varying radial and longitudinal pitches of weave such that unique configurations of the radially expanded mesh are formed when the inner member is moved relative to the outer member. In particular, the outer sleeve may be provided with a reduced radius portion made from a more tightly woven mesh. When expanded, the outer sleeve is "necked down" adjacent this reduced radius portion.

An actuating mechanism is coupled to the catheter tube and the inner tubular member so that they may be moved relative to each other. More particularly, actuation of the actuating member moves the inner member longitudinally relative to the catheter tube such that the outer sleeve is radially expanded into its predetermined configuration. This movement may expand the outer sleeve until it compresses against the inner walls of the vascular conduit or other body passageway. The actuating mechanism is preferably provided with a plurality of incremental or intermediate fixed positions which allow movement of the outer sleeve between a fully collapsed configuration to a fully expanded configuration. This allows opening of a flow passage within a vascular conduit through a continuous and incremental process. This configuration also allows use of a single balloon catheter within a variety of differing conduits.

In another aspect of the present invention, the proximal balloon end is connected to the inner tubular member proximally of the proximal sleeve end and the distal balloon end is connected to the inner tubular member distally of the distal sleeve end. The outer sleeve is not directly connected to the catheter but is centered over the balloon such that, when the balloon is inflated, a pair of annular balloon cavities (expanded balloon sections) are created on either side of the outer sleeve. The outer sleeve may be constructed of a tightly knit weave of filaments such that it is compressively retained on the balloon when the balloon is deflated as well as inflated. Since the expanded balloon sections are unrestrained by the outer sleeve, they may be inflated to a radial diameter much greater than that of the expanded outer sleeve.

A longitudinal passageway is provided through the inner tubular member and fluidly connected to an opening adjacent the outer sleeve. This passageway is used for dispensing a fluid capable of causing the dissolution of dissolving of the affected cells between the spaced apart and expanded balloon sections. The fluid may be a lysin. Alternatively, a vacuum may be drawn through the opening and passageway for the removal of obstructing material or previously applied fluid.

In another embodiment of the present invention, a surgical device for cleaning and removing occlusions from an artificial graft includes a catheter having a longitudinal axis extending between a proximal end and a distal end. An inflatable balloon, coaxial with the catheter, is coupled to the catheter adjacent a distal end. A tubular sleeve having a sleeve proximal end and a sleeve distal end surrounds the balloon. The sleeve is radially expandable and collapsible with the balloon and includes an irregular outer surface for contacting the graft. One end of the tubular sleeve is connected to the catheter to prevent its removal from the balloon.

The catheter further includes a longitudinal passageway having a distal opening for passage of a fluid into and out of the balloon. In addition, a second longitudinal passageway is provided within the catheter and includes an outlet or opening adjacent the balloon for dispensing a lysing agent into the vascular conduit.

A preferred method for enlarging a flow passage within a vascular conduit or other body passageway according to the principles of the present invention, comprises the steps of providing a balloon catheter which includes an inflatable balloon adjacent a distal end and a radially expandable and collapsible outer mesh sleeve which surrounds the balloon. The outer mesh sleeve is configured with an irregular outer surface for contacting the vascular conduit when it is radially expanded. The balloon catheter is then inserted within the vascular conduit. The balloon is then inflated such that the outer mesh sleeve contacts the inner walls of the vascular conduit. This expansion compresses the outer mesh sleeve against the inner walls of the vascular conduit. The balloon is then deflated and the balloon catheter removed from the vascular conduit.

In another aspect of the present invention, the method includes the step of radially expanding the mesh sleeve into a fixed configuration prior to the step of inflating the balloon. In this way, the balloon, when inflated, is restricted to the fixed configuration of the mesh sleeve. This prevents the balloon from overinflating and rupturing or otherwise damaging the vascular conduit. In addition, the fixed configuration may be a unique shape for particular use in enlarging the flow passage or alternatively for therapeutic treatment.

In yet another aspect of the present invention, the method includes the step of moving the balloon catheter within the vascular conduit or other body passageway. This step may be performed after the balloon is inflated such that the mesh sleeve is expanded against the inner walls of the vascular conduit and then rotated or moved longitudinally. This step moves the outer mesh sleeve, which may have an irregular outer surface, against the inner walls of the vascular conduit and enlarges the flow passage.

This invention, together with the additional features and advantages thereof, which is only summarized in the foregoing passages, will become more apparent to those of skill in the art upon reading the description of the preferred embodiments, which follows in the specification, taken together with the following drawings.

DESCRIPTION OF THE PREFERRED EMBODIMENTS

Figure 1:
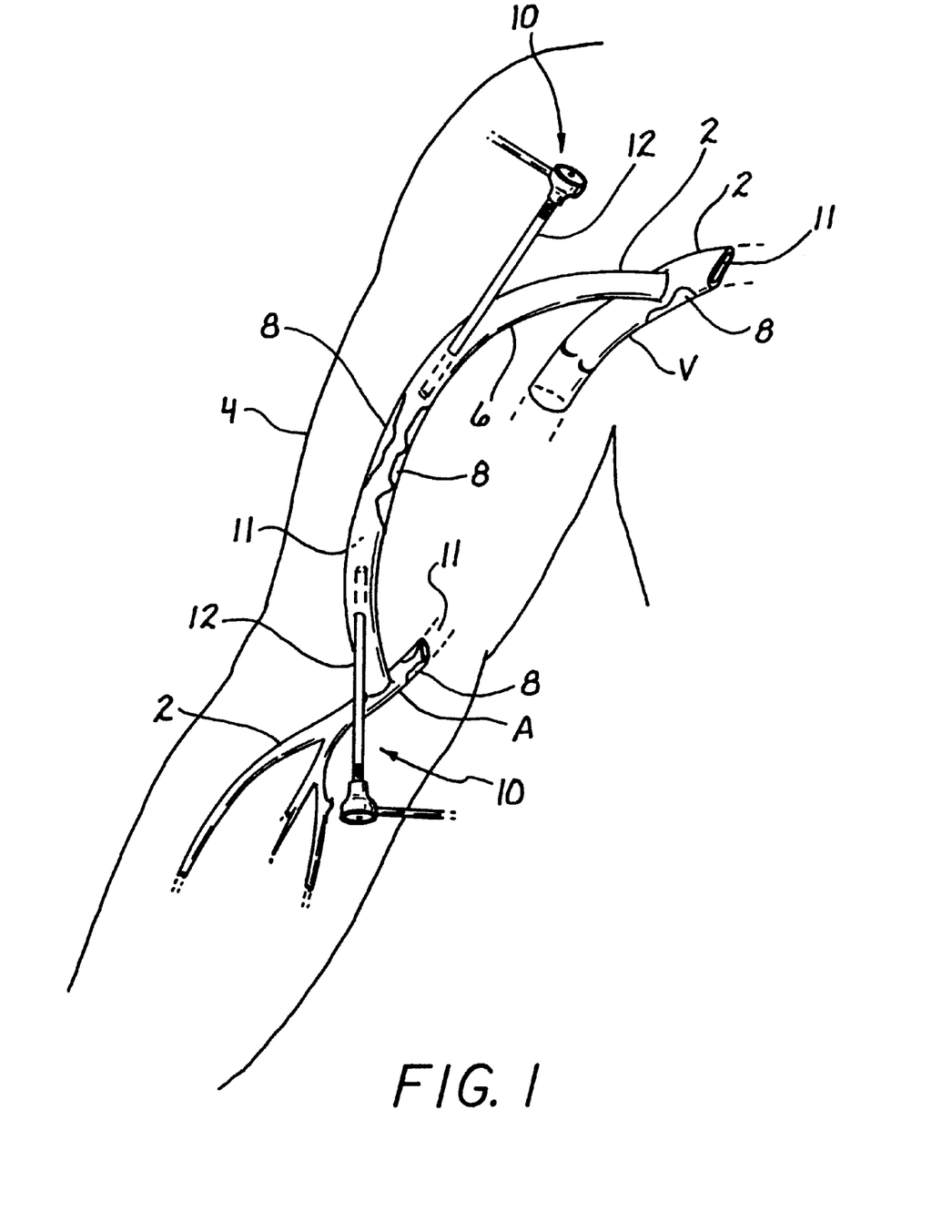
FIG. 1 is a diagrammatic view of an embodiment of the balloon catheter of the present invention shown inside a vascular conduit.

Referring now to the drawings, wherein like reference characters designate identical or corresponding parts throughout the several views and embodiments, a surgical device according to the principles of the present invention is illustrated in FIG. 1 and designated by the reference numeral 10. As shown, the surgical device 10 is inserted within a vascular conduit 2 of a patient 4. The vascular conduit 2, which may include an artificial or surgical graft 6 as shown, includes any vascular conduit 2 such as an artery, vein or other body conduit. An obstructing material 8 is shown occluding or otherwise obstructing a flow passage or passageway 11 within the vascular conduit 2.

Referring now to FIGS. 2 through 5, the surgical device 10 may include an elongate outer tube 12, which may be a catheter tube, having a longitudinal axis 13 which extends between a proximal end 14 and a distal end 16. An elongate inner member 18 may be provided to extend coaxially within the catheter tube 12. The inner member 18 may be configured with a slightly smaller cross-section or diameter than the catheter tube 12, such that a longitudinal passageway 20 is formed in the space between the inner member 18 and the catheter tube 12. Preferably, the inner member 18 is longitudinally slidable relative to the catheter tube 12. The construction, materials, and relative sizes of the catheter tube 12 and the inner member 18 are conventional and may be configured for each application as is known to those of skill in the art.

A balloon 22 is disposed coaxially about the inner member 18 to define an annular balloon chamber 24. The balloon 22 may comprise any sort of surgical or other balloon, including a bladder or similar inflatable device. Preferably, the balloon 22 is made from a distensible material, such as an elastomeric material, in a conventional fashion and as is known to those of skill in the art. Alternatively, the balloon 22 may be made from a nondistensible material. The balloon 22, in this embodiment, is constructed such that its outer periphery or surface is devoid of folds in either the deflated or relaxed condition or the inflated condition.

Figures 2, 3:
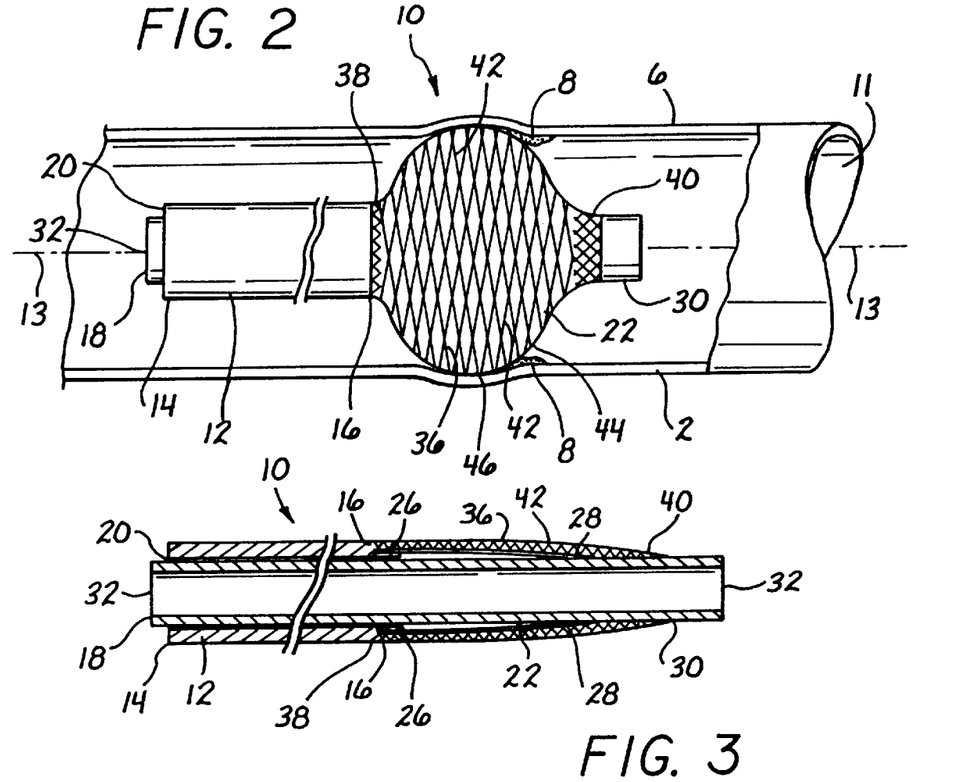
FIG. 2 is a diagrammatic view of the balloon catheter of FIG. 1 shown in a radially expanded configuration.
FIG. 3 is an axial cross-section view of the balloon catheter of FIGS. 1 and 2, illustrated in the collapsed configuration.
Figure 4:
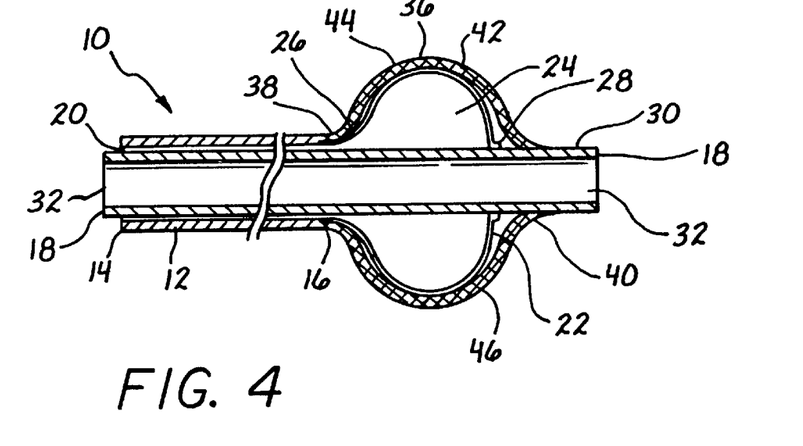
FIG. 4 is an axial cross-section view of the balloon catheter of FIGS. 1 and 2, illustrated in the expanded configuration.

The balloon 22 may be connected around the inner member 18 in a variety of configurations. For example, the balloon 22 may include a proximal balloon end 26 which is connected to the distal end 16 of the catheter tube 12. This connection is preferably a bonded or fused connection which is sealed as is known to those of skill in the art. However, any other method or device for structurally attaching and sealing the balloon 22 to the catheter 12 and inner member 18 may be used. In a like configuration, the opposing balloon end or distal balloon end 28 may be connected to the inner member 18 as is shown in FIGS. 3 and 4.

Figure 5:
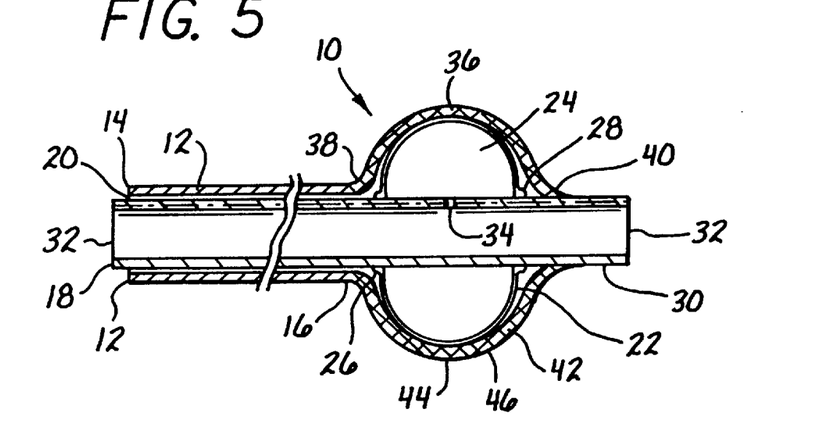
FIG. 5 is an axial cross-section view, similar to FIG. 4, of an alternative embodiment of the balloon catheter.
Figure 6:
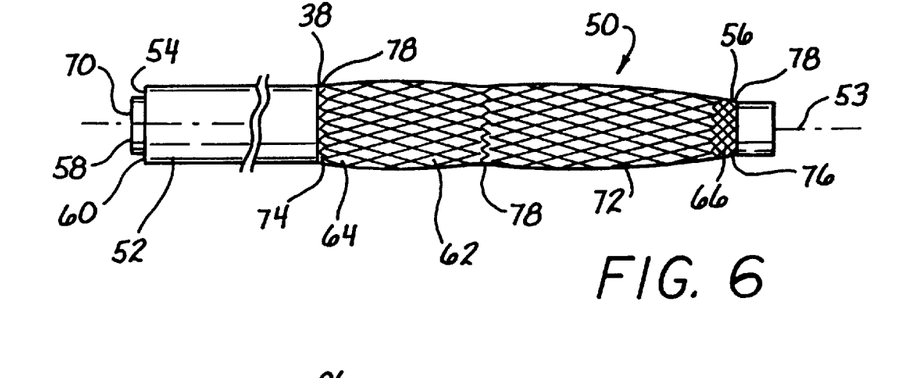
FIG. 6 is a side view of an alternative embodiment of the balloon catheter of the present invention shown in the collapsed configuration.

In an alternative configuration, both ends 26 and 28 of the balloon 22 may be directly connected to the inner member 18 as shown in FIG. 5. In this configuration, the inner member 18 is preferably an inner tubular member having an internal longitudinal passageway 32 which is fluidly connected with the annular balloon chamber 24. Preferably, the inner member 18 includes an opening or hole 34 which fluidly connects the longitudinal passageway 32 and the annular balloon chamber 24. In this way, a fluid may be passed through the inner tubular member 18 and through the opening 34 to inflate, or alternatively deflate the balloon 22.

An outer sleeve 36 is disposed coaxially about the balloon 22. The outer sleeve 36 includes a proximal sleeve end 38 and a distal sleeve end 40. Preferably, the proximal sleeve end 38 is connected to the distal end 16 of the catheter tube 12 and the distal sleeve end 40 is connected to the distal end 30 of the inner member 18. The outer sleeve ends 38 and 40 may be bonded, fused, clamped, or otherwise securely attached to the respective catheter tube 12 and inner member 18 to ensure a structurally secure connection.

The outer sleeve 36 may be made from a material that is both expandable and collapsible. Preferably, the outer sleeve 36 is movable from a fully collapsed configuration (FIG. 1) to an expanded configuration (FIG. 2). This expanding and collapsing of the outer sleeve 36 may be achieved through-longitudinal movement of the inner member 18 relative to the catheter tube 12 as will be described in greater detail below.

Preferably, the outer sleeve 36 comprises a woven mesh made from a filament 42 or plurality of filaments 42. The filaments 42 may be cross-helically wound, braided or otherwise woven into fingers such that the mesh is expandable and collapsible when moved longitudinally. Each specific filament 42 may be sized and cross-sectionally shaped to suit a particular function or purpose. For example, the filament 42 may have a round cross-section to provide for a relatively smooth outer surface 46 or a rectangular cross-section, including a sharp edge, which may provide a relatively abrasive or tractive outer surface 46. Increasing the diameter of the filament 42 may also be used to increase the irregularity of the outer mesh sleeve 36. Thus, the outer mesh sleeve 36 may be formed having a smooth outer surface 46 or alternatively, an abrasive or tractive outer surface 46.

The filament material 42 should be sufficiently strong that the balloon 22 is retained within the outer mesh sleeve 36. These materials may include wire, plastic, monofilament polyester, or any other material as is known to those of skill in the art. Combinations of differing materials may also be used. In addition to using different sizes, types and cross-sectional shapes of filaments 42, differing weaves or braids may also be used. Thus, the outer mesh sleeve 36 may be advantageously braided or woven such that each mesh may be collapsed to a minimum radial diameter and expanded for contacting the vascular conduit 2. In addition, the outer mesh sleeve 36 may have a specified limit of expansion such that the balloon 22 is prevented from further expansion, radially or axially, regardless of the amount of inflation pressure applied.

The outer sleeve 36, which may comprise a tubular mesh material having a plurality of meshes or openings, has a preselected maximum radial diameter or extension which limits the radial expansion of the balloon 22. In addition, the outer sleeve 36 may also include a preselected maximum axial extension or length to limit the axial expansion of the balloon 22. Preferably, the outer sleeve 36 comprises a length of woven or braided tubular fabric to form a mesh sleeve having a plurality of openings. Each of the openings may be individually expandable and collapsible to facilitate the expansion and collapsing, as well as shaping of the outer mesh sleeve 36. This outer mesh sleeve 36 may be made from filaments of plastic, metals or composites, and may form an irregular surface and even an abrasive surface as previously described.

When the inner member 18 is moved longitudinally or axially relative to the catheter tube 12, the outer sleeve 36 is also forced to move. For example, distal movement of the inner member 18 relative to the catheter tube 12 results in linear stretching or elongation of the outer sleeve 36 as well as radially collapsing or otherwise reducing the diameter of the outer sleeve 36. The maximum distal movement of the inner member 18 relative to the catheter tube 12 may be limited by the maximum elongated length of the outer sleeve 36. Alternatively, proximal longitudinal movement of the inner member 18, which shortens the distance between the distal ends 30 and 16 of the coaxial tubes 18 and 12, and results is a radial outward bulging of the outer sleeve 36. This radial outward bulging of the outer sleeve 36 is preferably sufficient for the outer sleeve 36 to contact the inner walls of the vascular conduit 2.

An actuating mechanism (not shown) may be coupled to both the catheter tube 12 and the inner member 18 in order to facilitate their relative movement. This actuating mechanism may include any apparatus and method for moving a first shaft relative to a second shaft or otherwise actuating the surgical device 10 as is known to those of skill in the art.

When the inner member 18 is moved proximally, along the longitudinal axis 13, relative to the catheter tube 12, the outer mesh sleeve 36 is radially expanded into a predetermined configuration 44 as shown in FIG. 2. This predetermined configuration 44 may be used solely to limit the maximum radial diameter of the inflated balloon 22 to prevent rupture or other damage to the vascular conduit 2. In a preferred embodiment, the surgical device 10, which may be a balloon catheter, is configured such that the inner member 18 is movable through a plurality of longitudinal positions relative to the catheter tube 12. Preferably, each of these positions is predetermined to radially expand the outer mesh sleeve 36 from a fully collapsed position (FIG. 1) into a plurality of predetermined configurations, such as the predetermined configuration 44. A lock, indent or other device for temporarily holding the inner member 18 in each of these predetermined positions (or predetermined configurations 44) relative to the catheter tube 12 may be provided. Preferably, these locks are provided on the actuating mechanism and are sufficiently strong to retain further expansion of the outer sleeve 36 when the balloon 22 is inflated. Each of the predetermined configurations 44 may be suited for a particular vascular conduit 2 or alternatively for incrementally enlarging the flow passage way 11.

Referring now to FIGS. 6 through 10, an alternative embodiment of a balloon catheter 50 according to the principles of the present invention will be described. Similar to that described in the previous embodiment, the balloon catheter 50 includes an elongate catheter tube 52 having a longitudinal axis 53 extending between a proximal end 54 and a distal end 56. An elongate inner tubular member 58 may be provided which extends coaxially within the catheter tube 52 and is longitudinally slidable relative to the catheter tube 52. The inner tubular member 58 is sized and configured such that a longitudinal passageway 60 is formed between the inner tubular member 58 and the catheter tube 52. The passageway 60 is sufficiently large for passage of a fluid therethrough.

A balloon 62 is disposed coaxially about the inner tubular member 58 as described in the previous embodiment. In particular, the balloon 62 includes a proximal balloon end 64 which is connected to the inner tubular member 58 and a distal balloon end 66 which is also connected to the inner tubular member 58, though distally of the proximal balloon end 64. A plurality of balloons 62 may also be used. In this configuration, each of the balloons 62 is spaced apart longitudinally along the inner tubular member 58. A second longitudinal passageway 70 may be provided through the inner tubular member 58 and fluidly interconnected with each of the balloons 62. This second longitudinal passageway 70 may be used for passage of a fluid such that each of the balloons 62 may be inflated and deflated in response to passage of the fluid therethrough. Each balloon 62 may be bonded, fused or otherwise connected to the inner tubular member 58, to form an annular balloon chamber 68, capable of inflation and deflation. Preferably, each balloon 62 is distensible and made from an elastomeric material as previously described. Alternatively, a non-distensible material may be used.

Figure 11:
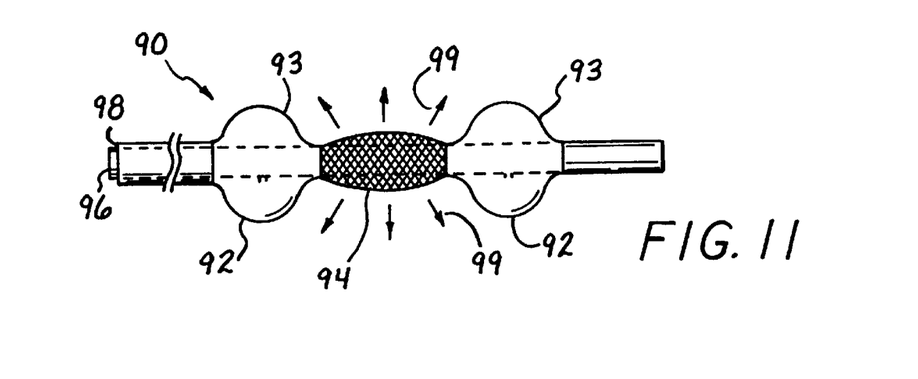
FIG. 11 is a side view of yet another alternative embodiment of the balloon catheter of the present invention shown in an expanded configuration.
Figure 12:
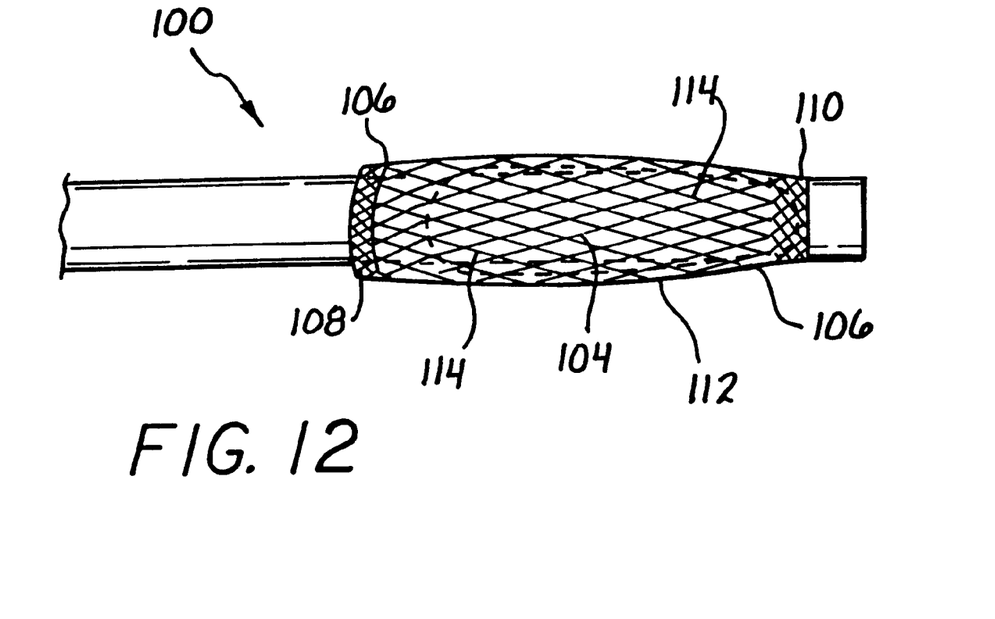
FIG. 12 is a side view of yet another alternative embodiment of the balloon catheter of the present invention shown in the collapsed configuration.
Figure 13:
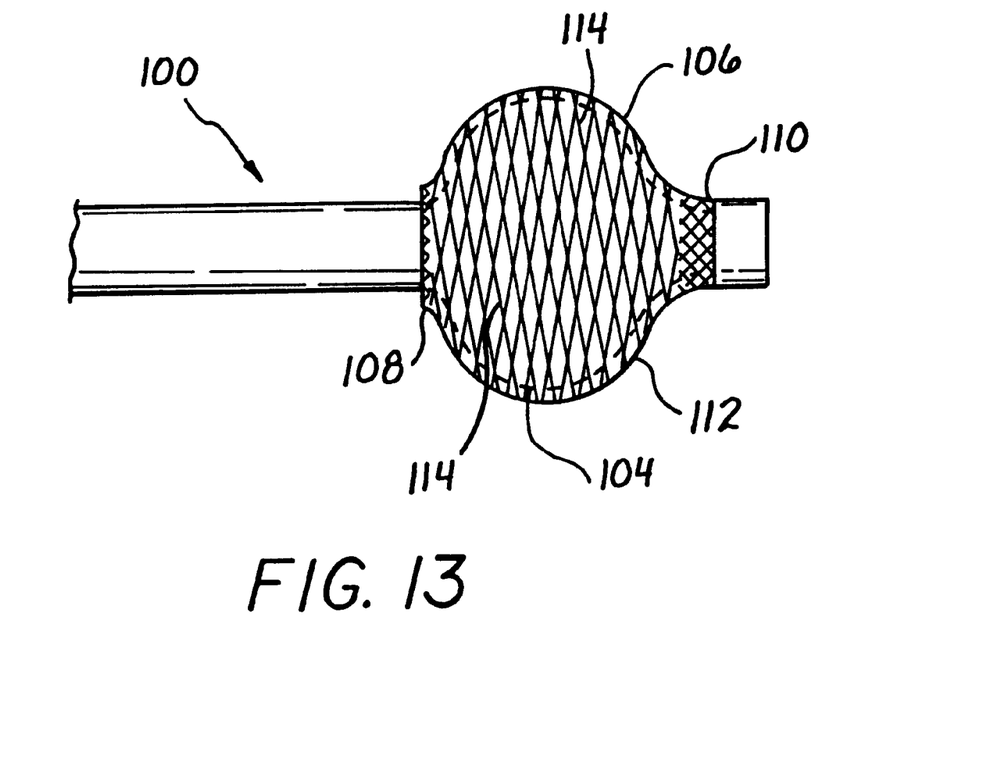
FIG. 13 is a side view of the balloon catheter of FIG. 12 shown in an expanded configuration.

An outer sleeve 72, capable of restricting the expansion and shape of the inflated balloon 62, includes a proximal sleeve end 74 and a distal sleeve end 76. The proximal sleeve end 74 may be connected to the distal end 56 of the catheter tube 52 and the distal sleeve end 76 may be connected to the inner tubular member 58. These connections may be similar to those described for the previous embodiment. Preferably, the outer mesh sleeve 72 surround the balloon 62 and is radially expandable through relative longitudinal sliding between the inner tubular member 58 and the catheter tube 52, also as described for the previous embodiment. Alternatively, the outer mesh sleeve 72 may only surround a central portion (reduced radius portion 78) to define a plurality of balloons 62 (FIG. 11).

Figure 8:
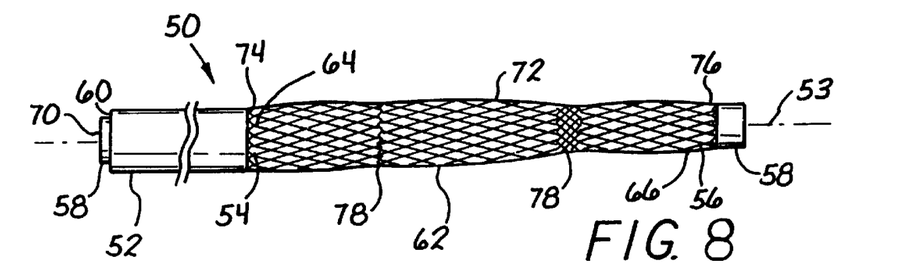
FIG. 8 is a side view of yet another alternative embodiment of a balloon catheter of the present invention shown in the collapsed configuration.
Figure 9:
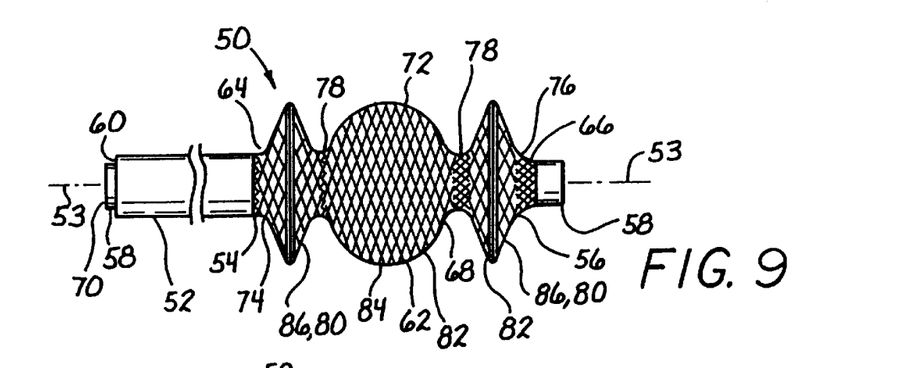
FIG. 9 is a side view of the balloon catheter of FIG. 8 shown in a radially expanded configuration.
Figure 10:
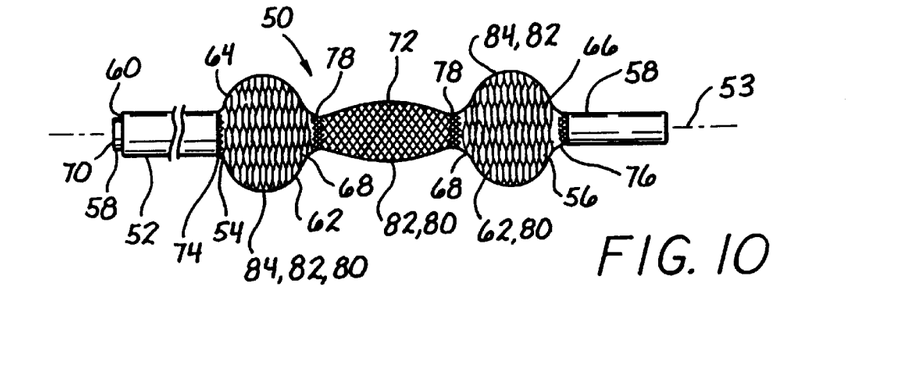
FIG. 10 is a side view of another alternative embodiment of the balloon catheter of the present invention shown in an expanded configuration.

The outer mesh sleeve 72 may also include a reduced radius portion 78 which restricts its radial expansion. The outer sleeve 72 may advantageously be configured with one (FIGS. 6 and 7) or a plurality of reduced radius portions 78 (FIGS. 8 through 10). The reduced radius portions 78 restrict the allowable expansion of the outer mesh sleeve 72, thus creating a plurality of annular chambers 80 on either side of the reduced radius portion 78. The outer mesh sleeve 72 defining each annular chamber 80 may be configured such that it is expandable to a plurality of predetermined configurations 82 as previously described. The outer mesh sleeve 72 is preferably similar to that described for the previous embodiment.

In a preferred embodiment, the reduced radius 78, is formed from a portion of the outer mesh sleeve 72 which has a tighter mesh pattern. This tighter mesh pattern, which may include a tighter weave or additional woven fibers, restricts the expansion of the mesh within the reduced radius portion 78. Alternatively, the reduced radius portion 78 may comprise a second mesh sleeve or any other over-structure which surrounds a portion of the outer mesh member 72. Thus, the reduced radius portion 78 may include a plastic or metal band surrounding the outer mesh sleeve 72.

When the inner tubular member 58 is moved proximally relative to the catheter tube 52, the outer mesh sleeve 72 is expanded radially outward as previously described. The outer mesh sleeve 72 may comprise a specially configured weave or braid such that, when expanded, it is formed into a predetermined configuration 82. In a similar fashion, incremental longitudinal movement of the inner tubular member 58 relative to the catheter tube 52, between a plurality of predetermined positions, may be used to form the outer mesh sleeve 72 into a number of predetermined configurations 82. A lock or detent may be provided at each predetermined position to temporarily secure the inner tubular member 58 relative to the catheter tube 52.

Figure 7:
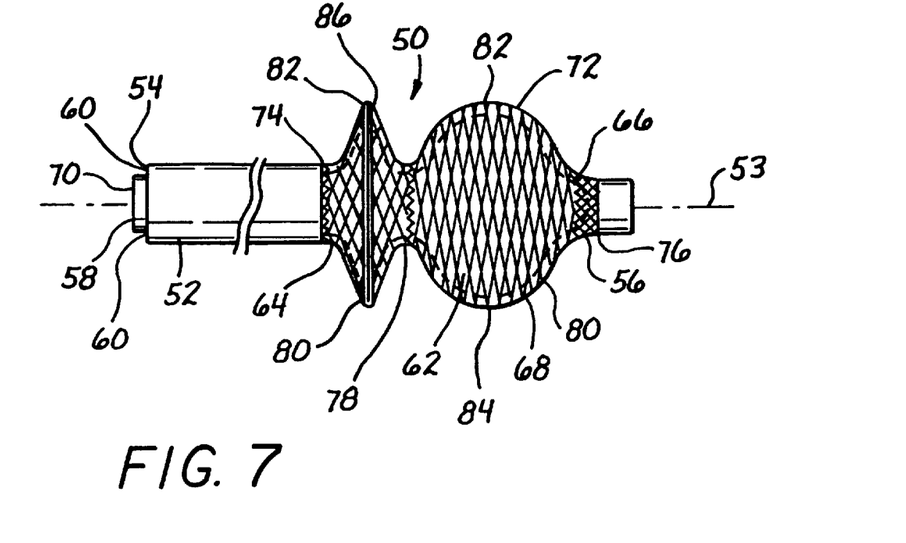
FIG. 7 is a side view of the balloon catheter of FIG. 6 shown in a radially expanded configuration.

Each of the predetermined configurations 82, preferably defines a unique shape as shown in FIGS. 7, 9 and 10. These unique shapes 80 may advantageously include a spherical shape 84, a cone shape 86 as well as most any other shape to which the outer mesh sleeve 72 may be expanded. The balloon 62 may be inflated to conform to the expanded outer mesh sleeve 72. A distensible balloon 62 is preferred because of its ability to better conform. The balloon 62 may also be inflated to assist in the expansion of the outer mesh sleeve 72 into the predetermined configuration 82. However, the outer mesh sleeve 72, once fully expanded into the predetermined configuration 82, retains the balloon 62 from further radial and/or axial expansion. Thus, the balloon 62 is advantageously retained from rupturing or otherwise damaging the vascular conduit 2.

Referring now to FIG. 11, another alternative embodiment of a balloon catheter 90 will be described. In this embodiment, The balloon catheter 90 is similar to those of previous embodiments, and will thus only be described generally where necessary to explain their differences.

The balloon catheter 90 includes two primary enlargements 92 which may be spaced apart. These enlargements 92 preferably comprise a catheter balloon or a plurality of catheter balloons 93 similar to that previously described. An over-structure or outer mesh sleeve 94 may be provided between the primary enlargements 92 as shown in FIG. 11. In this configuration, the outer mesh sleeve 94 may be made from a rigid mesh, or alternatively as relatively non-expanding mesh. Alternatively, the outer mesh sleeve 94 may be provided over both primary enlargements 92, as best shown in FIG. 10, and includes expansive outer portions. Each of the primary enlargements 92 is inflatable and deflatable through use of a fluid passed through a longitudinal passageway 96 within the balloon catheter 90.

A second longitudinal passageway 98 within the balloon catheter 90 provides a conduit for the dispensing of a fluid 99, or alternatively the application of a vacuum 99, through the outer mesh structure 94. Preferably, the fluid 99 or vacuum 99 is applied between each of spaced apart primary enlargements 92. In a preferred embodiment, the fluid 99 may include a lysing agent which is used to assist in the removal of any obstructing material 8 within the vascular conduit 2. Alternatively, the fluid 99 may include any therapeutic agent as is known to those of skill in the art. Suction or a vacuum 99 may be provided in the region between the primary enlargements 92 to promote adherence of any obstructing material 8 to the associated outer mesh sleeve 94 or alternatively, to facilitate the removal of any other material between the primary enlargements 92.

Referring now to FIGS. 1, 2, 12 and 13, an alternative embodiment of a balloon catheter according to the principles of the present invention will be described. In this embodiment, the balloon catheter 100 may be advantageously used for cleaning and removing obstructions from within a surgical graft 6, artificial vascular graft, shunt or similar surgical conduit, best illustrated in FIGS. 1 and 2. In particular, the balloon catheter 100 is advantageously configured for removing thrombi or clots within the surgical graft 6. The balloon catheter 100, which may be a conventional balloon catheter having a conventional balloon 104 also includes an expandable and collapsible outer tubular sleeve 106. This outer sleeve 106, which may be similar to the outer sleeve 36 described in a previous embodiment, includes a proximal sleeve end 108 and a distal sleeve end 110 and surrounds the balloon 104. The outer sleeve 106 is radially expandable and collapsible with the inflation and deflation of the balloon 104 of the balloon catheter 100.

The outer sleeve 106 may be coupled at either its proximal sleeve end 108 or its distal sleeve end 110 to the balloon catheter 100. In this configuration, one end 108, 110 of the outer sleeve 106 is allowed to freely slide along the balloon catheter 100 and the balloon. Thus, the expansion of the balloon 104 may shorten the longitudinal length of the outer sleeve 106, while deflation of the balloon 104 may lengthen the sleeve 106. The outer sleeve 106 may be coupled to the balloon 104 to ensure the outer sleeve 106 collapses when the balloon 104 is deflated. If coupled to the balloon 104, the attachment is preferably through a reduced radius portion or necked down portion on the end 108, 110 of the outer sleeve 106 which is not connected to the balloon catheter 100.

In this configuration, the outer sleeve 106 may be expanded with the inflated balloon 104 to most any radial dimension the balloon 104 is capable. However, the outer sleeve 106 may be configured with a sufficiently rigidity or a sufficiently tight mesh, as previously described, such that expansion of the balloon 104, radially or axially, is restrained.

The outer sleeve 106 may be advantageously configured with an irregular outer surface 112. Since a surgical graft 6 is tougher than a natural vascular conduit 2 and capable of more intense scrubbing, the irregular outer surface 112 may be substantially more abrasive than that previously described. In this configuration, the outer sleeve 106 may be made from a plurality of filaments 114, woven or braided into a mesh, as described for previous embodiments. Similarly, the filaments 114 may be sized, shaped and oriented to adjust the irregularity or abrasiveness of the outer surface 112. Alternatively, the outer sleeve 106 may be made from any expandable sleeve which has an irregular outer surface.

When the balloon 104 is inflated, the outer sleeve 106 is expanded radially outward, along with the inflating balloon, until the outer surface 112, which may be a woven or braided mesh defining an irregular outer surface, is forced against the inner walls of the vascular conduit 2 or surgical graft 6. When adjacent a thrombus or other obstruction, the irregular outer surface 112 of the outer sleeve 106 may be pushed into the obstruction. A fluid such as a lysing agent, may be dispensed, or a vacuum drawn, within the surgical graft 6 and adjacent the outer sleeve 106. The balloon catheter may then be moved or rotated to free the obstruction and open the flow path. The balloon 104 may then be deflated such that the outer sleeve 106 is collapsed and the balloon catheter 100 removed from the graft 6.

Referring now to FIGS. 1–11, a method of using the balloon catheter 10 of the present invention will be described. The method, which enlarges the flow passage way 11 within the vascular conduit 2, includes the step of providing a catheter, such as the balloon catheter 10 previously described. The provided balloon catheter 10 includes a radially expandable and collapsible outer mesh sleeve 36 which surrounds the balloon 22. The outer mesh sleeve 36 is independently expandable and collapsible relative to the balloon 22 for contacting the vascular conduit 2 when the sleeve 36 is expanded. The balloon catheter 10 is then inserted into the vascular conduit 2 adjacent the obstructing material 8. The outer mesh sleeve 36 may then be radially expanded into the predetermined configuration 44.

The step of radially expanding and forming the mesh outer sleeve 36 into a predetermined configuration 44 may be accomplished by longitudinally moving the inner member 18 proximally relative to the catheter tube 12. The predetermined configuration 44 may include a predetermined shape such as one previously described. After the outer mesh sleeve 36 has been expanded into the predetermined configuration 44, the balloon 22 may then be inflated such that the outer mesh sleeve 36 is radially expanded sufficiently to contact the inner walls of the vascular conduit 2. The outer mesh sleeve 36 prevents the balloon 22 from radially expanding beyond the predetermined configuration 44.

The balloon catheter 10 may then be moved within the vascular conduit 2 to open the flow passageway 11. This movement may include longitudinally sliding the expanded sleeve 36 against the vascular conduit 2 or alternatively rotating the outer sleeve 36. A fluid 99 may be infused or otherwise dispensed into the vascular conduit 2 adjacent the outer mesh sleeve 36. This fluid 99 preferably comprises a cell dissolving or dissolution agent, such as a lysin, as previously described but may also contain other types of treatment fluids. Alternatively, or in conjunction with the dispensed fluid 99, a vacuum or reduced pressure may be drawn adjacent to the mesh outer sleeve 36.

After enlarging the flow passageway 11 or otherwise removing any obstructing material 8 from within the vascular conduit 2, the balloon 22 may be deflated. Once the balloon 22 is deflated, the outer mesh sleeve 36 may be collapsed and the balloon catheter 10 may be removed from the vascular conduit 2.

It will be understood that various modifications can be made to the various embodiments of the present invention herein disclosed without departing from the spirit and scope thereof. For example, various sizes of the balloon catheter and the outer mesh sleeve are contemplated as well as various types of construction materials. Also, various modifications may be made in the configuration of the parts and their interaction. Therefor, the above description should not be construed as limiting the invention, but merely as an exemplification of preferred embodiments thereof Those of skill in the art will envision other modifications within the scope and spirit of the present invention as defined by the claims appended hereto.

What is claimed is:

1. A surgical device for controlling the expansion and shape of a body conduit, said surgical device comprising:

an outer tube having a longitudinal axis extending between a proximal end and a distal end;

an inner member extending coaxially within said outer tube, said inner member longitudinally slidable within said outer tube and configured such that a longitudinal passageway is created between said inner member and said outer tube for passage of a fluid therethrough;

a balloon disposed coaxially about said inner member, said balloon having a proximal balloon end connected to said distal end of said outer tube and a distal balloon end connected to said inner member to define an annular balloon chamber in fluid connection with said longitudinal passageway, said balloon having properties for inflating and deflating in response to the fluid passing through the longitudinal passageway; and an outer sleeve surrounding said balloon, said sleeve having a proximal sleeve end connected to said distal end of said outer tube and a distal sleeve end connected to the distal end of said inner member such that said outer sleeve is radially expandable and collapsible independent of said balloon through movement of the inner member relative to the outer tube.

2. The balloon catheter as recited in claim 1 wherein said inner member is longitudinally movable within said outer tube such that said outer sleeve may be radially expanded into a predetermined configuration and said balloon, upon inflation, is limited to the predetermined configuration by said outer sleeve.

3. A balloon catheter for enlarging a flow passage within a vascular conduit, said balloon catheter comprising:

a catheter tube having a longitudinal axis extending between a proximal end and a distal end;

an inner member extending coaxially within said catheter tube, said inner member being longitudinally slidable within said catheter tube and being configured such that a longitudinal passageway is created between said inner member and said catheter tube for passage of a fluid therethrough;

a balloon disposed coaxially about said inner member, said balloon having a proximal balloon end connected to said distal end of said catheter tube and a distal balloon end connected to said inner member to define an annular balloon chamber in fluid connection with said longitudinal passageway, said balloon having properties for inflating and deflating in response to the fluid passing through the longitudinal passageway; and an outer sleeve disposed about said balloon, said sleeve having a proximal sleeve end connected to said distal end of said catheter tube and a distal sleeve end connected to said inner member such that said outer sleeve is radially expandable and collapsible independent of said balloon through movement of the inner member relative to the catheter tube.

4. The balloon catheter as recited in claim 3 wherein said balloon is distensible.

5. The balloon catheter as recited in claim 3 wherein said inner member is longitudinally movable within said catheter tube such that said outer sleeve may be radially expanded into a predetermined configuration and said balloon, upon inflation, is limited to the predetermined configuration by said outer sleeve.

6. The balloon catheter as recited in claim 5 wherein the predetermined configuration of the outer sleeve is one of a plurality of predetermined configurations, each associated with one of a plurality of predetermined positions of the inner member relative to the catheter tube.

7. The balloon catheter as recited in claim 5 wherein each of said predetermined configurations is associated with one of a plurality of different shapes.

8. The balloon catheter as recited in claim 7 wherein at least one of the unique shapes comprises a pair of spaced apart annular chambers.

9. The balloon catheter as recited in claim 8 wherein said outer sleeve comprises a reduced radius portion between said spaced apart annular sections.

10. The balloon catheter as recited in claim 5 wherein said predetermined configuration comprises a pair of spaced apart annular chambers.

11. The balloon catheter as recited in claim 3 wherein, said fluid is a first fluid, and said inner member comprises an axial passageway for passage of a second fluid.

12. The balloon catheter as recited in claim 3 wherein said outer sleeve comprises a tubular woven mesh.

13. The balloon catheter as recited in claim 12 wherein said woven mesh comprises a plurality of interlaced filaments.

14. A balloon catheter for enlarging a flow passage in a body conduit, said catheter comprising:

a catheter tube having a longitudinal axis extending between a proximal end and a distal end;

an inner tubular member disposed coaxially within said catheter tube, said inner tubular member being longitudinally slidable within said catheter tube and configured to provide a longitudinal passageway between said inner tubular member and said catheter tube for passage of a fluid therethrough;

a balloon disposed coaxially about said inner tubular member, said balloon having a proximal balloon end connected to said distal end of said catheter tube and a distal balloon end connected to said inner tubular member to define an annular balloon chamber; and an outer sleeve surrounding said balloon, said sleeve having a proximal sleeve end connected to said distal end of said catheter tube and a distal sleeve end connected to said inner member such that said outer sleeve is radially expandable and collapsible independent of said balloon through movement of the inner member relative to the catheter tube.

15. The balloon catheter as recited in claim 14 wherein said inner tubular member comprises a longitudinal passageway in fluid connection with said annular balloon chamber for fluidly inflating and deflating said balloon.

16. The balloon catheter as recited in claim 15 said balloon is distensible.

17. The balloon catheter as recited in claim 15 wherein said inner tubular member is longitudinally movable relative to said catheter tube such that said outer sleeve may be radially expanded into a predetermined configuration and said balloon, upon inflation, being limited to said predetermined configuration by said outer sleeve.

18. The balloon catheter as recited in claim 17 wherein the predetermined configuration of the outer sleeve is one of a plurality of predetermined configurations, each associated with one of a plurality of predetermined positions of the inner member relative to the catheter tube.

19. The balloon catheter as recited in claim 18 wherein each of said predetermined configurations is associated with one of a plurality of different shapes.

20. The balloon catheter as recited in claim 14 wherein said outer sleeve comprises a mesh of woven filaments.

21. A surgical device for cleaning and removing obstructions from a vascular conduit, said surgical device comprising:

a catheter having a longitudinal axis extending between a proximal end and a distal end;

an inflatable and deflatable balloon, coaxial with said catheter and coupled to said catheter adjacent said distal end of said catheter; and an outer tubular sleeve surrounding said balloon and having a sleeve proximal end and a sleeve distal end, said sleeve being radially expandable independent of said balloon and having an irregular outer surface for contacting said vascular conduit; and at least one of said sleeve proximal end and said sleeve distal end being coupled to said catheter.

22. The surgical device as recited in claim 21 wherein said catheter further comprises an opening at said distal end and wherein said opening is in fluid connection with said balloon for passing a fluid through said catheter to inflate and deflate said balloon.

23. The surgical device as recited in claim 22 wherein the fluid is a first fluid and said catheter further comprises a second longitudinal passageway for passage of a second fluid through said catheter, said second longitudinal passageway being in fluid connection with a second opening for dispensing of said second fluid exteriorly of said balloon.

24. The surgical device as recited in claim 23 wherein said fluid is a lysing agent.

25. The surgical device as recited in claim 21 wherein said proximal sleeve end is attached to the distal end of said catheter.

26. The surgical device as recited in claim 21 wherein said proximal sleeve end is attached to the catheter proximally of the distal end and said distal sleeve end is longitudinally movable relative to said catheter distal end.

27. The surgical device as recited in claim 21 wherein said outer tubular sleeve comprises a woven filament mesh.

28. The surgical device as recited in claim 21 wherein said balloon is formed of a distensible material.

29. A balloon catheter for enlarging a flow passage within a vascular conduit, said balloon catheter comprising:

a catheter tube having a longitudinal axis extending between a proximal end and a distal end;

an inner member extending co-axially within said catheter tube, said inner member being longitudinally slidable within said catheter tube;

a balloon disposed co-axially about said inner member, said balloon having a proximal balloon end connected to said distal end of said catheter tube and a distal balloon end connected to said inner member to define at least one annular balloon chamber having properties for inflating and deflating in response to a fluid passing through the catheter tube; and an outer sleeve disposed about said balloon, said sleeve having a proximal sleeve end connected to said distal end of said catheter tube and a distal sleeve end connected to said inner member, the outer sleeve being radially expandable independent of said balloon through movement of the inner member relative to the catheter tube to a predetermined configuration including a pair of spaced-apart annular chambers.

30. A method for using a balloon catheter to enlarge a flow passage within a body conduit, said method comprising the steps of:

providing a catheter having an inflatable balloon and an expandable outer mesh sleeve disposed about said balloon;

inserting said catheter into the vascular conduit;

expanding the mesh into contact with the vascular conduit;

independently of the expanding step, inflating the balloon into contact with the expanded mesh sleeve;

deflating the balloon;

contracting the mesh sleeve; and removing the balloon catheter from the vascular conduit.

31. The method of enlarging the body conduit as recited in claim 30, and further comprising the step of radially expanding the woven mesh sleeve into a predetermined configuration prior to the step of inflating said balloon, such that when inflated, the balloon is limited to the predetermined configuration of the mesh sleeve.

32. The method of enlarging a vascular conduit as recited in claim 31, and further comprising the step of moving said balloon catheter within said vascular conduit after said step of inflating such that said woven mesh sleeve is expanded against the vascular conduit and abrades said vascular conduit.

33. The method of enlarging a vascular conduit as recited in claim 31, and further comprising the step of infusing a lysing agent adjacent said woven mesh sleeve when said balloon catheter is in said vascular conduit.

34. The method of enlarging the body conduit as recited in claim 32, wherein:

the expanding step includes the step of expanding the sleeve to a predetermined configuration; and the inflating step includes a step of limiting the shape of the balloon to the predetermined configuration of the mesh sleeve.

35. A method for removing an obstruction from a vascular conduit comprising the steps of:

providing a balloon catheter having a radially expandable woven mesh sleeve disposed about a distensible balloon and a pair of coaxial tubular shafts comprising an inner shaft and an outer shaft, wherein said inner shaft is coupled to a distal end of the mesh sleeve and said outer shaft is coupled to a proximal end of said mesh sleeve such that movement of said inner shaft relative to said outer shaft expands and collapses said woven mesh sleeve;

inserting the balloon catheter into the vascular conduit;

directing the catheter along the vascular conduit until the mesh sleeve is disposed adjacent the obstruction;

moving the inner shaft relative to the outer shaft to enlarge said mesh sleeve into a predetermined configuration;

inflating said balloon to expand the balloon to the predetermined configuration of the woven mesh sleeve;

moving the catheter with the mesh sleeve against the obstruction to remove at least a portion of the obstruction from the vascular conduit;

deflating the balloon to collapse the balloon within the vascular conduit;

moving the inner shaft relative to the outer shaft to collapse said woven mesh sleeve; and removing the balloon catheter from the vascular conduit.

36. The method for removing an obstruction as recited in claim 35, further comprising the step of infusing a liquid into said vascular conduit adjacent said woven mesh sleeve.

37. A method for cleaning a flow passage within an artificial graft conduit comprising the steps of:

providing a balloon catheter having an inflatable inner balloon and a coaxial woven mesh sleeve surrounding said balloon, said inner balloon being inflatable to expand said mesh sleeve against said vascular graft;

placing the balloon catheter within said artificial vascular graft conduit;

expanding the mesh sleeve into contact with the vascular graft;

independently of the expanding step, inflating the balloon into contact with the mesh sleeve;

deflating the balloon to facilitate the independent collapse of the mesh sleeve; and removing the balloon catheter from the artificial graft conduit.

38. The method for cleaning a flow path within an artificial graft conduit as recited in claim 37, further comprising the step of moving the expanded mesh sleeve within the vascular graft conduit.

39. The method for cleaning a flow path within an artificial graft conduit as recited in claim 37, further comprising the step of infusing a lysing agent within the vascular graft conduit.

* * * * *